United States Patent
Schelhaas et al.

(10) Patent No.: US 6,414,192 B1
(45) Date of Patent: Jul. 2, 2002

(54) PROCESS FOR PREPARING 4-AMINODIPHENYLAMINE

(75) Inventors: Michael Schelhaas, Köln; Carl Casser, Berlin; Dietmar Bielefeldt, Ratingen; Pieter Ooms, Krefeld; Joachim Haider, Köln; Manfred Jautelat, Burscheid; Christian Laue, Monheim; Henry Giera, Grosskitzingen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/007,014

(22) Filed: Nov. 6, 2001

(30) Foreign Application Priority Data

Nov. 8, 2000 (DE) .......................... 100 55 221

(51) Int. Cl.$^7$ ............................... C07C 209/00
(52) U.S. Cl. .................. 564/420; 564/416; 564/423; 564/422
(58) Field of Search ................. 564/416, 420, 564/423, 422

(56) References Cited

U.S. PATENT DOCUMENTS

| | | | |
|---|---|---|---|
| 4,129,740 A | 12/1978 | Zengel et al. | 560/48 |
| 4,187,248 A | 2/1980 | Merten et al. | 260/576 |
| 4,187,249 A | 2/1980 | Maender et al. | 260/576 |
| 4,665,232 A | 5/1987 | Podder et al. | 564/406 |
| 4,670,595 A | 6/1987 | Podder et al. | 564/406 |
| 5,925,791 A | 7/1999 | Buysch et al. | 574/416 |
| 5,994,584 A | * 11/1999 | Ooms et al. | |

FOREIGN PATENT DOCUMENTS

| | | |
|---|---|---|
| DE | 1 147 237 | 4/1963 |
| WO | 93/24450 | 12/1993 |

OTHER PUBLICATIONS

Kirk–Othmer Encyclopedia of Chemical Technology, 4$^{th}$ edition, (month unavailable) 1992, vol. A3, pp. 424–456, Antioxidants.

Ullmann's Encyclopedia of Industrial Chemistry, 5$^{th}$ edition, vol. A3, (month unavailable) 1985, pp. 91–111, Peter P. Klemchuk, Antioxidants.

* cited by examiner

*Primary Examiner*—Samuel Barts
(74) *Attorney, Agent, or Firm*—Joseph C. Gil; Noland J. Cheung

(57) ABSTRACT

The invention provides a process for preparing 4-aminodiphenylamine, an important starting product for synthesizing antioxidants and stabilizers in the rubber and polymer industry, by hydrogenating nitrosobenzene with hydrogen in the presence of a proton acid as catalyst and in the presence of a hydrogenating catalyst, optionally in the presence of an inert organic solvent and thermally decomposing the 4-ADPA ammonium salt produced in this way, wherein 4-ADPA is obtained.

4-aminodiphenylamine is produced in good yields and high purity by the process according to the present invention. Furthermore, no effluent is produced, which makes the process particularly economic and ecological.

5 Claims, No Drawings

PROCESS FOR PREPARING 4-AMINODIPHENYLAMINE

FIELD OF THE INVENTION

The invention provides a process for preparing 4-aminodiphenylamine (4-ADPA), an important starting product for synthesizing antioxidants and stabilizers in the rubber and polymer industry (Kirk-Othmer, Encyclopedia of Chemical Technology, 4th edition, 1992, Vol. A3, pages 424–456; Ullman's Encyclopedia of Industrial Chemistry, 5th edition, Vol. A3, 1985, pages 91–111).

BACKGROUND OF THE INVENTION 4-aminodiphenylamine can be prepared using a variety of methods. One possibility is the two-step (intermediate product 4-nitrodiphenylamine) reaction of aniline or aniline derivatives with p-chloronitrobenzene in the presence of an acid acceptor or a neutralizing agent and optionally in the presence of a catalyst. Preparation using this method is described, for example, in DE-A 3 501 698, DE-A 1 856 63, U.S. Pat. No. 4,670,595, U.S. Pat. No. 4,187,249 and U.S. Pat. No. 4,187,248. A disadvantage of this process is that the halide ions being produced have to be disposed of at considerable cost and the starting materials such as p-chloronitrobenzene or the corresponding formanilide derivatives have to be prepared in additional reaction steps.

Another possibility for preparing 4-ADPA comprises the reaction of aniline or corresponding aniline derivatives with nitrobenzene in the presence of tetraalkylammonium hydroxides and in the presence of regulated amounts of protic material (see WO 95/00324 and WO 93/24250). The disadvantage in this case is the low thermal stability of tetraalkylammonium hydroxides, so these cannot be fully recycled to the process.

The one-step preparation of 4-ADPA from nitrobenzene or nitrosobenzene in the presence of hydrogen, a hydrogenating catalyst and in the presence of bases provides only unsatisfactory yields 4-ADPA (see DE-A 19 70 91 24 and DE-A 19 734 055).

Another possibility for preparing 4-ADPA comprises the acid-catalyzed dimerization of nitrosobenzene to 4-nitrosophenyl-diphenyl-hydroxylamine followed by reduction to 4-ADPA (see DE-A 1 147 237 and DE-A 2 703 919). The disadvantage of this process is the isolation of thermally unstable 4-nitrosophenyl-phenylhydroxylamine which is required and the effluent optionally produced by neutralization.

SUMMARY OF THE INVENTION

The present invention provides a process for preparing 4-ADPA which is characterized in that nitrosobenzene is hydrogenated with hydrogen in the presence of a proton acid as catalyst and in the presence of a hydrogenation catalyst, optionally in the presence of an inert organic solvent, and the 4-ADPA ammonium salt thus produced is thermally decomposed, wherein 4-ADPA is produced.

DETAILED DESCRIPTION OF THE INVENTION

Proton acids which are suitable for the process according to the present invention are aliphatic and aromatic sulfonic acids such as methanesulfonic acid and benzenesulfonic acid, hydrogen fluoride and trifluoroacetic acid. The yield of 4-ADPA generally decreases with increasing water content of the acids according to the present invention, so the use of anhydrous acids is preferred. The acids are preferably used according to the present invention in amounts of 0.1 to 100, preferably 1 to 100 mol per mol of nitrosobenzene. The acids may be used either individually or in the presence of each other.

Hydrogenation catalysts, which are suitable for the process according to the present invention are virtually all heterogeneous catalysts which are known to be hydrogenation catalysts. Catalysts according to the present invention include metals from the 8th–10th groups of the Periodic System (according to IUPAC, new) or copper and/or chromium on suitable supports with a metal content of 0.01 to 50 wt. %, preferably 0.1 to 20 wt. %, with respect to the total weight of catalyst. According to the present invention, catalysts may be used which contain one or more of the metals mentioned above. Preferred metals are platinum, palladium and rhodium, more preferably, platinum and palladium. Further preferred catalysts are Raney nickel and supported nickel catalysts. According to the present invention, the metals mentioned above, or their compounds, may also be used in the pure form as solids. Palladium black and platinum black may be mentioned as examples of a metal in the pure form.

Catalysts according to the present invention may be used in amounts of 0.01 to 20 wt. %, with respect to the nitrosobenzene used, preferably in amounts of 0.01 to 10 wt. %, in batchwise process variants. When performing the reaction in a continuous manner, for example in a stirred tank with powdered catalysts or in the trickle phase on fixed bed catalysts, loads of 0.01 to 500 g of nitrosobenzene per g of catalyst and per hour are used.

The reaction temperatures for the process according to the present invention are −20° C. to 50° C., preferably −10° C. to 30° C.; the hydrogen pressure is 0.1 to 150 bar, preferably 0.5 to 70 bar, most preferably 1 to 50 bar.

The process according to the present invention may also be performed in the presence of organic solvents. Aprotic solvents, which are inert to the proton acid used and under the hydrogenation conditions are preferred. Suitable inert organic aprotic solvents are aliphatic or aromatic hydrocarbons, linear or cyclic ethers, halogenated aliphatic or aromatic hydrocarbons or their mixtures. The following may be mentioned as suitable solvents: benzene, toluene, xylene, tert.-butyl methyl ether, dioxan, tetrahydrofuran, chloroform, methylene chloride and/or chlorobenzene. The amount of solvent used in the process according to the present invention is not critical. Suitable amounts may also easily be determined by appropriate preliminary trials. In the case of continuous addition of nitrosobenzene and catalyst acid, the amount of solvent used depends in particular on the solubility of nitrosobenzene in the solvent used.

The process according to the present invention may be performed either continuously or batchwise. When using a batchwise procedure, the proton acid is added to the nitrosobenzene, optionally in the presence of a solvent, and the reaction mixture obtained is then hydrogenated with hydrogen in the presence of a hydrogenation catalyst. Continuous process variants may be performed in equipment known to a person skilled in the art for bringing solid, liquid and gas phases into contact. Stirred tanks, forced circulation reactors, bus reactors, bubble columns operated in cocurrent or countercurrent mode or trickle phase reactors or cascades of these reactors are suitable.

Isolation of the 4-aminodiphenylamine from the acid reaction mixture is performed in such a way that water is added to the reaction mixture, the mixture is neutralized with a base and then optionally extracted with an organic solvent. According to the present invention, a preferred mode of working-up the reaction mixture comprises working up the reaction mixture by distillation after filtering off the hydrogenation catalyst. In this way, the proton acid used and optionally the solvent used can be virtually quantitatively recycled. No effluent is produced in the process according to the present invention, which is of great economic and ecological advantage.

The 4-ADPA salt of the corresponding proton acids remaining is decomposed thermally at temperatures of about 50 to 200° C. and pressures of 1013 to 0.05 bar in order to obtain 4-ADPA.

EXAMPLES

Example 1

In an autoclave, 21.4 g nitrosobenzene and 1 g Pd/C (5%) are added to 100 ml of anhydrous hydrofluoric acid at 0° C. The reaction mixture is heated to 10° C. and then hydrogenated under a 30 bar pressure of hydrogen. After filtering off the hydrogenation catalyst, the catalyst acid (hydrofluoric acid) is distilled off. The 4-ADPA ammonium salt remaining is decomposed thermally at 200° C. and 16 mbar, wherein 17 g of 4-ADPA with a fluoride content of <0.1% are obtained.

Example 2

100 ml of trifluoroacetic acid are used as catalyst acid using the same procedure as in Example 1. The 4-ADPA ammonium salt obtained is thermally decomposed at 100° C. and 1 mbar, wherein 15 g of 4-ADPA are obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing 4-aminodiphenylamine (4-ADPA), comprising the step of hydrogenating nitrosobenzene with hydrogen in the presence of a proton acid as catalyst and in the presence of a hydrogenation catalyst, optionally in the presence of an inert organic solvent to form an 4-ADPA ammonium salt which is then thermally decomposed to obtain 4-ADPA.

2. A process according to claim 1, wherein hydrogenation is performed at temperatures of −20° C. to 50° C. and pressures of 0.1 to 150 bar.

3. A process according to claim 1, wherein the thermal decomposition of 4-ADPA ammonium salt is performed at temperatures of 50 to 200° C. and pressures of 1013 to 0.05 mbar.

4. A process according to claim 1, wherein said proton acids are aliphatic and aromatic sulfonic acids, hydrogen fluoride or trifluoroacetic acid.

5. A process according to claim 1, wherein said organic solvents are aliphatic or aromatic hydrocarbons, linear or cyclic ethers, halogenated aliphatic or aromatic hydrocarbons or their mixtures.

* * * * *